(12) United States Patent
Martens et al.

(10) Patent No.: US 10,746,712 B2
(45) Date of Patent: Aug. 18, 2020

(54) PROCESS FOR CALIBRATING A GAS SENSOR AND FOR THE SUBSEQUENT USE OF THE CALIBRATED GAS SENSOR

(71) Applicant: Drägerwerk AG & Co. KGaA, Lübeck (DE)

(72) Inventors: Matthias Martens, Groß Schenkenberg (DE); Hans-Ullrich Hansmann, Barnitz (DE); Kai Einecke, Berkenthin (DE); Rainer Buchner, Ratzeburg (DE); Hannes Sturm, Ahrensburg (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 199 days.

(21) Appl. No.: 15/981,122

(22) Filed: May 16, 2018

(65) Prior Publication Data

US 2018/0335410 A1    Nov. 22, 2018

(30) Foreign Application Priority Data

May 17, 2017    (DE) .......................... 10 2017 004 727

(51) Int. Cl.
    *G01N 33/00*    (2006.01)
(52) U.S. Cl.
    CPC ................ *G01N 33/0006* (2013.01)
(58) Field of Classification Search
    CPC .. G01N 33/0006; G01N 33/007; G01N 21/09; G01N 21/3504; G01M 3/2807
    See application file for complete search history.

(56) References Cited

U.S. PATENT DOCUMENTS

| | | | | |
|---|---|---|---|---|
| 2,353,287 | A * | 7/1944 | Benesh | G01M 3/2807 73/40.5 R |
| 4,384,925 | A | 5/1983 | Stetter et al. | |
| 6,119,710 | A * | 9/2000 | Brown | G01F 1/50 137/14 |
| 6,237,392 | B1 * | 5/2001 | Yu | G01N 1/22 73/1.06 |
| 6,632,674 | B1 | 10/2003 | Warburton | |
| 7,406,854 | B2 * | 8/2008 | Lange | G01N 21/09 73/1.06 |
| 7,645,367 | B2 * | 1/2010 | Tschuncky | G01N 33/0006 204/401 |

(Continued)

FOREIGN PATENT DOCUMENTS

| | | |
|---|---|---|
| DE | 232 763 A1 | 2/1986 |
| DE | 295 21 224 U1 | 11/1996 |

(Continued)

*Primary Examiner* — Helen C Kwok
(74) *Attorney, Agent, or Firm* — McGlew and Tuttle, P.C.

(57) ABSTRACT

A process for operating a gas sensor (10), which process includes a calibration of the gas sensor (10). A test gas (16) is drawn in via a pump (12) coupled with the gas sensor (10), whereby the test gas (16) is supplied to the gas sensor (10). Different volume flows are generated by the pump (12) and respective volume flow-dependent measured values (26) are detected by the pump (12). The volume flow-dependent measured values (26) are recorded together with the respective volume flow. A sensor control unit and a computer program functioning as a control program (48) are provided to implement the process.

20 Claims, 5 Drawing Sheets

(56) References Cited

U.S. PATENT DOCUMENTS

| | | | |
|---|---|---|---|
| 2007/0062249 A1* | 3/2007 | Forrest | G01N 33/0006 |
| | | | 73/1.06 |
| 2011/0197649 A1 | 8/2011 | Han et al. | |
| 2018/0143171 A1* | 5/2018 | Hansmann | G01M 3/2807 |

FOREIGN PATENT DOCUMENTS

| | | |
|---|---|---|
| DE | 601 02 837 T2 | 9/2004 |
| DE | 10 2010 015994 A1 | 9/2011 |
| EP | 1 992 945 A2 | 11/2008 |
| WO | 2007/087403 A2 | 8/2007 |

* cited by examiner

PROCESS FOR CALIBRATING A GAS SENSOR AND FOR THE SUBSEQUENT USE OF THE CALIBRATED GAS SENSOR

CROSS REFERENCE TO RELATED APPLICATIONS

This application claims the benefit of priority under 35 U.S.C. § 119 of German Application 10 2017 004 727.8, filed May 17, 2017, the entire contents of which are incorporated herein by reference.

FIELD OF THE INVENTION

The present invention pertains to a process for operating a gas sensor, namely, to a process for calibrating the gas sensor and for the subsequent use of the calibrated gas sensor.

BACKGROUND OF THE INVENTION

A process for calibrating a gas sensor is known from US 2011/0197649 A1. Provisions are made there for a volume, in which a gas to be measured is circulated through a gas sensor by means of a pump, to be able to be closed by means of a plurality of valves. The closed volume guarantees known conditions as the basis for calculating a concentration.

Processes for calibrating a gas sensor, which are based, in brief, on the release of a known quantity of substance, are described in WO 2007/087403 A2 and U.S. Pat. No. 6,632,674 B1.

In prior-art, so-called diaphragm-controlled gas sensors, the measured signal of the gas sensors depends on the transportation of a substance through a diaphragm of the gas sensor. The diaphragm and its sealing elements separate the sensor system proper and an electrolyte in the interior of the sensor from a respective measured gas and prevent the escape of the electrolyte up to a pressure difference determined by the construction.

Typical calibration processes predefine a certain test gas concentration and check whether the sensor calculates a measured value that is correct in a broad range. A difference between a resulting expected value based on the known test gas concentration and the respective measured value is used here for the correction. The test gas concentration is ideally in a range to be monitored during the operation of the gas sensor or is subject to normative requirements.

A changing pressure acting on the separating diaphragm of the gas sensor leads to a pressure-dependent passage of substance through the diaphragm (increased passage of substance at high pressure; reduced passage of substance at low pressure). Therefore, gas sensors whose principle of function is based on a concentration-dependent passage of substance, therefore show elevated measured values at high pressure. Pressure changes that markedly influence (distort) the measured values of a gas sensor are frequently caused by a pump, which transports the gas to be measured to the gas sensor via a rather long feed line (for example, tube). Such a pump often comprises a rotatingly driven, elastic chamber volume or a piston-and-cylinder unit, both of which operate cyclically and consequently cause cyclical pressure variations.

In addition to the pressure change, which leads to a distorted measured value, a change in the gas concentration is another source of error. The calibration of a gas sensor is adapted to an essentially stagnant medium in an area (gas space) in front of the diaphragm. A so-called depletion layer with a lower concentration of the gas to be measured develops in the immediate vicinity of the diaphragm in a stagnant medium. The molecules to be measured, which pass through the diaphragm due to the concentration gradient, are missing on the opposite side of the diaphragm and are equalized by diffusion from the gas space in a short time. There is a lower concentration directly in front of the diaphragm than in the gas to be measured. If energy is now introduced into the space directly in front of the diaphragm, this concentration stratification is changed. The input of energy results, for example, from a motion of the gas caused by a (varying) volume flow.

The respective prevailing pressure and/or volume flow conditions consequently influence the measurement result. On the one hand, an incorrect measured value is displayed. On the other hand, a change in concentration is displayed, even though the gas concentration has remained the same.

SUMMARY OF THE INVENTION

An object of the present invention is correspondingly to provide a process with which such errors can be minimized or at least reduced.

This object is accomplished according to the present invention by a process for operating a gas sensor as well as by means of a device and system operating according to that process. The process comprises a calibration of the gas sensor (calibration process) as well as the use of the calibration, i.e., the use of the calibrated gas sensor (measurement process).

Provisions are made in the calibration process according to the invention, i.e., in a chronologically first part of the process for operating a gas sensor, for drawing in a test gas by means of a pump connected fluidically to the gas sensor and for delivering the test gas to the gas sensor, for generating different volume flows by means of the pump and for detecting respective volume flow-dependent measured values (measured gas values) by means of the gas sensor and for the volume flow-dependent measured values to be recorded together with the respective volume flow, i.e., with a value (volume flow value) coding the respective volume flow, for example, with a measured volume flow value detected by a sensor or with a set point used to actuate the pump, for a later use.

The data detected within the framework of the calibration process, namely, pairs of measured gas values and volume flow values, form the basis for the calibration of a measured gas value detected later during the measuring operation by means of the gas sensor. The data detected within the framework of the calibration process as well as data optionally resulting therefrom will hereinafter be called calibration basis for short.

A measured value supplied by the gas sensor, on the one hand, and an effective volume flow are detected in a second part of the process, which follows the calibration process, i.e., is a chronologically later part, namely, during a measuring operation of the gas sensor. The detection of the measured value (measured gas value) by means of the gas sensor as well as the detection of a value coding the respective volume flow takes place in exactly the same way as during the calibration process. The measured gas value detected during the measuring operation is corrected based on the data of the calibration basis. The measured gas value detected during the measuring operation is corrected here on the basis of the detected volume flow, which is the effective volume flow during the detection of this measured gas value, as well as on the basis of the volume flow-dependent measured gas values determined within the framework of the calibration process.

Consequently, measured gas values are detected in different situations, namely, during the calibration process, on the one hand, and during the later measuring operation, on the other hand, and respective corresponding volume flow values, which code a volume flow that is effective during the detection of the respective measured gas value, are detected within the framework of the process according to the invention for operating a gas sensor. The measured gas values are at times called calibration measured gas values for distinction if they are detected within the framework of the calibration process, and they are called operation measured gas values if they are detected during the measuring operation. This also applies to the measured volume flow values, which are sometimes called correspondingly calibration measured volume flow values and operation volume flow values.

Using this terminology, the process according to the invention can be described as follows: To calibrate the gas sensor, a test gas is drawn in by means of a pump coupled with the gas sensor and fed to the gas sensor. Different volume flows are generated by means of the pump and calibration volume flow values are detected. Respective volume flow-dependent calibration measured gas values are detected during the action of different volume flows by means of the gas sensor. For example, correction factors or a calibration function is determined as a calibration basis on the basis of the volume flow-dependent calibration measured gas values and of the corresponding calibration volume flow values. The data of the calibration basis are used during the subsequent measuring operation of the gas sensor. An operation measured gas value supplied by the gas sensor, i.e., a current measured value, and an operation volume flow value that is effective during the detection of the operation measured gas value are now detected. The operation measured gas value is corrected on the basis of the operation volume flow value as well as on the basis of the volume flow-dependent calibration measured gas value. This correction is carried out, for example, by using the calibration function or the correction factors to calibrate the detected operation measured gas value, namely, for example, by determining, as a function of the operation volume flow value, a correction factor best fitting this operation volume flow value or a value of the calibration function belonging to this correction factor and by calibrating the operation measured gas value with this.

In the interest of a better comprehensibility of the following description, it will be continued with the more concise terms "measured value" and "volume flow value." Depending on the particular factual context, calibration measured gas value or operation measured gas value as well as calibration volume flow value or operation volume flow value shall be imputed for the terms.

It should be noted that the measuring operation does not necessarily follow the calibration process immediately. A pause between the calibration process and the measuring operation is not actually important. The calibration process may optionally be carried out more often, for example, regularly at predefined or predefinable times if the pause between the detection of a measured value during the measuring operation and the calibration process is too great or if there is even a reason to assume that the pause to the calibration is too long.

The advantage of the calibration process being provided is that by recording the volume flow-dependent measured values (volume flow-dependent calibration measured gas values) together with the respective volume flow (calibration volume flow values), the actual dependence of the measured values supplied by the gas sensor on the respective volume flow is detected. Due to the volume flow-dependent measured values being detected together with the respective volume flow, it is possible to use the volume flow-dependent measured values or a respective representation of the volume flow-dependent measured values, for example, a look-up table or a polynomial, during a later measuring operation on the basis of a respective, then effective volume flow.

The calibration process is preferably carried out when the respective gas sensor and the pump associated therewith are in a real installation situation, because the particular volume flow effective at the gas sensor is influenced not only by the respective pumping capacity of the pump, but also by a tube or pipeline section, with which the pump and the gas sensor are fluidically coupled, as well as by a tube or pipeline section, with which the test gas is drawn in, and by a tube or pipeline section, through which the test gas is discharged Calibration under the conditions of the respective installation situation consequently yields measured values with which an especially accurate calibration is possible.

In a process for using a gas sensor calibrated according to the principle according to the invention, a measured value (original measured value; operation measured gas value) and an effective volume flow (operation volume flow) are detected during the operation of the gas sensor. The detected original measured value is then corrected on the basis of the detected effective volume flow and the volume flow-dependent measured values determined within the framework of the calibration process. The gas sensor then outputs the corrected measured value as a measured value for the detected gas concentration.

In one embodiment of such a process for using a gas sensor calibrated according to the principle according to the invention, a calibration basis determined on the basis of the volume flow-dependent measured values determined within the framework of the calibration process, for example, a calibration function, is selected on the basis of the detected volume flow (operation volume flow value); in particular, one of a plurality of calibration bases, for example, one of a plurality of calibration functions, namely, the calibration basis or calibration function that best fits the detected volume flow (operation volume flow value), is selected on the basis of the detected volume flow. The detected original measured value (operation measured gas value) is then corrected on the basis of the selected calibration basis or calibration function. The gas sensor then outputs the corrected measured value as a measured value for the detected gas concentration.

The calibration process and the subsequent correction of a measured value (operation measured gas value) detected during the measuring operation of the gas sensor as well as subsequently described embodiments of the calibration process as well as of the correction of the measured value and the process steps comprised thereby are carried out automatically, i.e., without a special intervention on the part of a user of the gas sensor. The automatic execution of the process takes place under the control of a control unit, especially of a control unit associated with the gas sensor or with the pump. This control unit comprises a processor in the form of or in the manner of a microprocessor as well as a memory. A control program executable by the processor, which program is carried out by the processor thereof during the operation, is or can be loaded into the memory. Operating actions of the user in connection with the process are limited, for example, to the starting of the calibration process and/or to the provision of the test gas.

The above-mentioned object is correspondingly also accomplished by means of a control unit, which operates according to the process as here and hereinafter described and comprises for this means for carrying out the process. The present invention is preferably implemented in software. The present invention is thus, on the one hand, also a computer program functioning as a control program with program code instructions executable by a computer, and, on the other hand, a storage medium with such a computer program, i.e., a computer program product with program code means as well as, finally, also a device in the form of a system with a gas sensor and with a pump fluidically connected to the gas sensor as well as with a control unit, in whose memory such a computer program is or can be loaded as a means for carrying out the process and embodiments thereof.

Provisions are made in an embodiment of the calibration process for generating initially a volume flow corresponding to a predefined starting value to generate different volume flows by means of the pump and for increasing or decreasing the volume flow starting from the starting value until a predefined target value is reached. Compared to the more general form of the process, which makes basically only provisions for generating different volume flows by means of the pump in, for example, a random or quasi-random manner, this creates defined and easily reproducible conditions.

Provisions are made in another embodiment of the calibration process for the volume flow to be increased or decreased starting from the starting value at a predefined or predefinable increment until the target value is reached. Such a stepwise (incremental) increase or decrease in the volume flow reduces the amount of data generated within the framework of the calibration process. A volume flow-dependent measured value (calibration measured gas value) and the corresponding volume flow (calibration volume flow value) are detected for a volume flow corresponding to the starting value and the target value. A volume flow-dependent measured value (calibration measured gas value) and the corresponding volume flow (calibration volume flow value) each are detected once again between them after each stepwise increase or decrease in the volume flow. Even though a discrete curve rather than a continuous curve describing the dependence of the respective measured values supplied by the gas sensor on the volume flow is thus obtained, this is sufficient as a basis for an interpolation of intermediate values. If an especially high accuracy is required, the increment can be correspondingly adapted (reduced), and correspondingly more volume flow-dependent measured values and a respective corresponding volume flow are correspondingly detected at a reduced increment.

In a special embodiment of the calibration process, the starting value for the volume flow is greater than the target value, and the volume flow is correspondingly reduced starting from the starting value, in particular it is reduced stepwise at a predefined or predefinable increment, until the target value is reached. The corresponding gas concentration will then become established more rapidly at the sensor due to the flushing of the dead space brought about in the course of the process in the tube or pipeline section with the initially larger volume flow.

A calibration function is determined automatically, for example, by a polynomial interpolation, which is known, in principle, per se, in another embodiment of the calibration process on the basis of the volume flow-dependent measured values (calibration measured gas values) and of the respective corresponding volume flow (calibration volume flow value). A calibration factor can be determined directly for correcting the measured value (operation measured gas value) supplied originally by the gas sensor by means of the calibration function during the subsequent measuring operation for each volume flow (operation volume flow value) then obtained by introducing the volume flow into the calibration function.

Provisions are correspondingly made in a process for using a gas sensor calibrated by means of a calibration process of the type being here and hereinafter described for detecting a measured value originally supplied by the gas sensor during the operation of the gas sensor (operation measured gas value) and a respective effective volume flow (operation volume flow value) and for correcting the detected measured value (operation measured gas value) on the basis of the detected effective volume flow (operation volume flow value) and of the volume flow-dependent measured values (calibration volume flow values) determined within the framework of the calibration process.

In a special embodiment of this process for using a gas sensor calibrated according to the principle being described here, the correction of the measured value supplied originally by the gas sensor is carried out on the basis of a calibration function determined within the framework of the calibration process.

An exemplary embodiment of the present invention will be explained in more detail below on the basis of the drawings. Mutually corresponding objects or elements are designated by the same reference numbers in the figures.

The exemplary embodiment or each exemplary embodiment shall not be considered to represent a limitation of the present invention. Variants and modifications, especially variants and combinations that the person skilled in the art can identify in respect to accomplishing the object, for example, through a combination or modification of individual features that are described in connection with the general or special part of the specification and are contained in the claims and/or in the drawings, are rather possible within the framework of the present disclosure. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
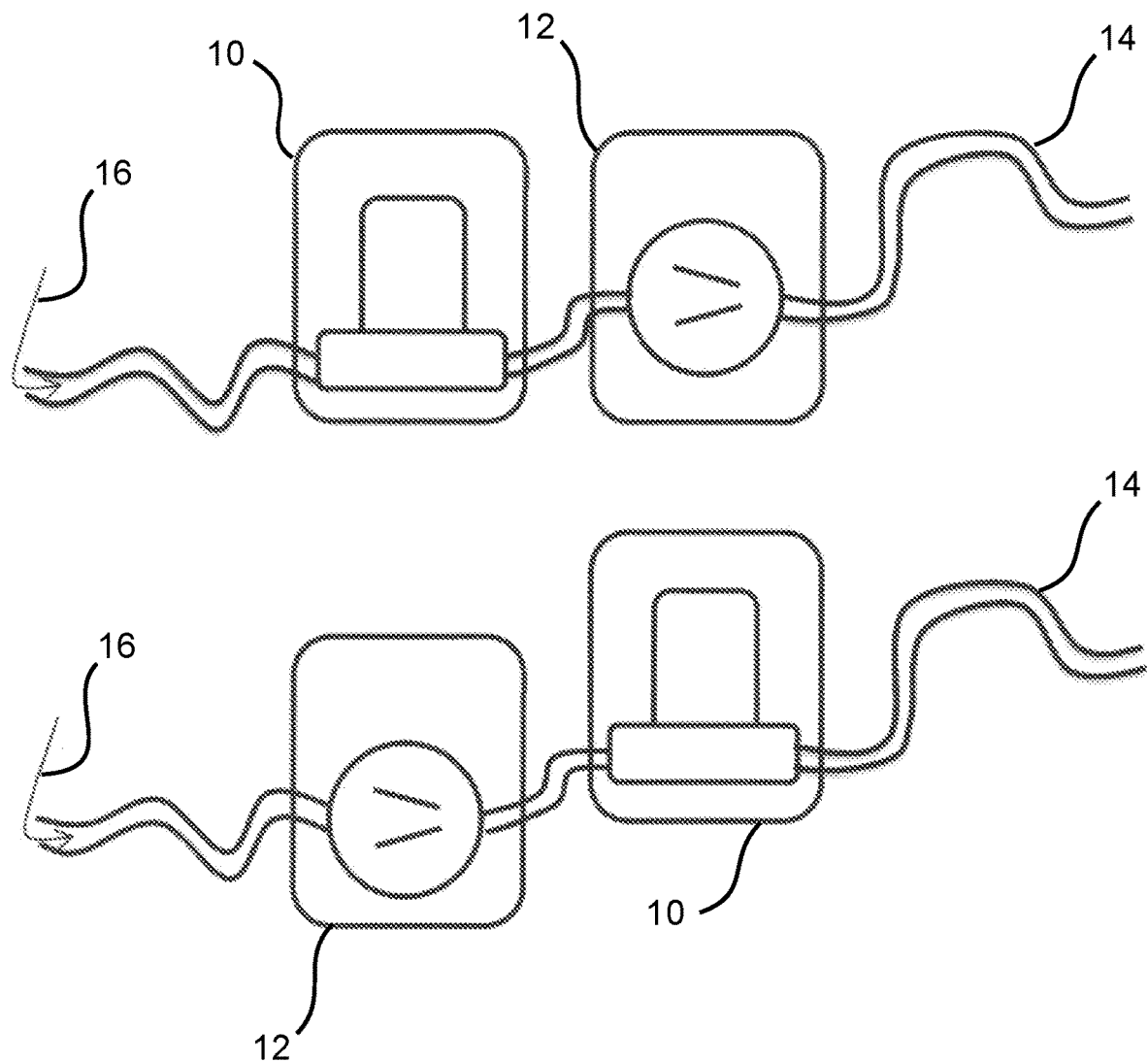
FIG. 1 is a schematic view showing a gas sensor and a pump, in two different configurations, wherein a test gas or a gas to be measured is fed by means of the pump to the gas sensor.

Referring to the drawings, in a highly simplified form, the view in FIG. 1 schematically shows a system with a gas sensor 10 and with a pump 12 in two different configurations. The gas sensor 10 and the pump 12 are connected together (coupled fluidically) in a tube system 14. A measured or test gas 16 is drawn in through the tube system 14 and is transported to the gas sensor 10 based on the pump 12 located either upstream or downstream of the gas sensor 10.

Figure 2:
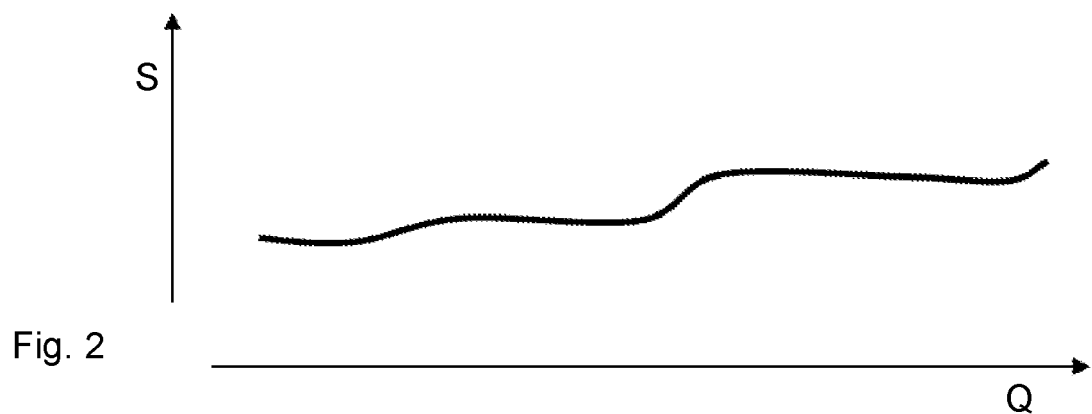
FIG. 2 is a graph showing a fictitious dependence of a measured signal of the gas sensor on a volume flow through the gas sensor.

The view in FIG. 2 shows a fictitious dependence of a measured signal S of the gas sensor 10 on a volume flow Q through the gas sensor 10, namely, on the volume flow Q generated by means of the pump 12. The volume flow Q is plotted in the view in FIG. 2 on the abscissa and the measured signal S of the gas sensor 10 on the ordinate.

Figure 3:
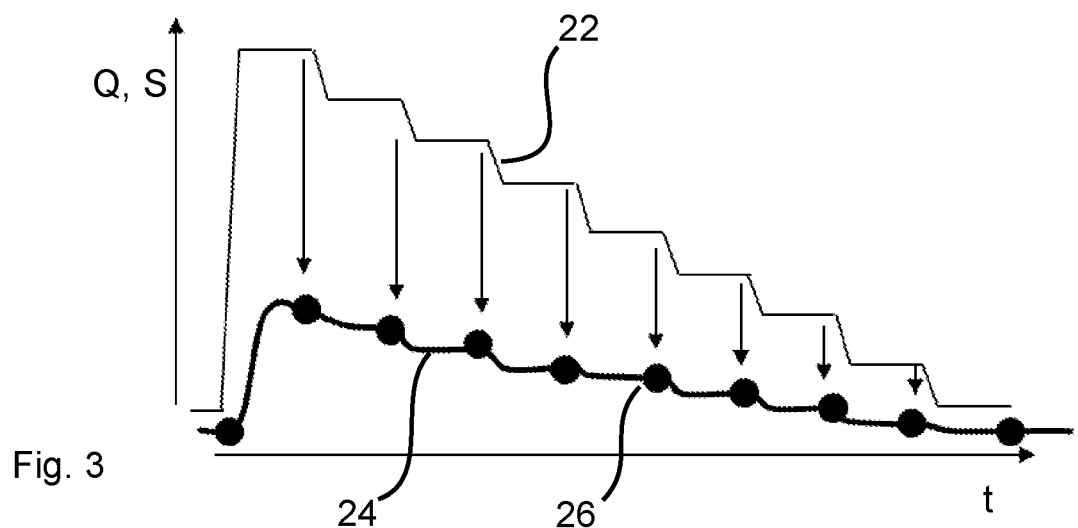
FIG. 3 is a graph showing a measured value curve during the calibration process according to the invention.

The view in FIG. 3 shows the course of a calibration process 20 (FIG. 5) according to the invention over the time t. The two graphs show a curve of the volume flow Q (volume flow curve 22) and a measured value curve 24, namely, a curve of the measured signal S of the gas sensor 10, wherein individual measured values 26 of the gas sensor 10 are highlighted in the measured value curve 24. It can be seen on the basis of the volume flow curve 22 that the volume flow Q is reduced stepwise within the framework of the calibration process 20 from an initial value to a target value. The reduction takes place at a predefined or predefinable increment. Starting from the starting value and after each reduction, the volume flow Q is maintained at a constant value over a predefined or predefinable time period. The detection (measurement) of a measured value 26 (calibration measured gas value) of the gas sensor 10 takes place during this period of a constant volume flow Q (volume flow plateau). The individual measured values 26 are graphically highlighted on the measured value curve 24 in the view shown in FIG. 3.

A dependence of the measured values 26 (calibration measured gas values) on the particular volume flow Q (calibration volume flow value) is clearly recognizable in the measured value curve 24. A volume flow-dependent correction factor 28 is obtained within the framework of the calibration on the basis of a particular volume flow Q and of a corresponding measured value 26. The expansion of the correction factor 28 is shown in the view in FIG. 4 as a correction factor curve 30 as a function of the volume flow Q. A calibration function 32 is obtained from all the correction factors 28, for example, by a simple interpolation or a polynomial interpolation on the basis of the correction factors 28.

The calibration function 32 or the underlying correction factors 28 are used during the calibration of a measured value 26 (operation measured gas value) supplied by the gas sensor 10 during the later measuring operation. The calibration function 32 or the underlying correction factors 28 acts/act as a calibration basis. Depending on a volume flow Q (operation volume flow value) prevailing during the measuring operation, a correction factor 28 best fitting this volume flow Q or a value of the calibration function 32 belonging to this volume flow Q is determined, and this correction factor value or calibration function value is linked, for example, multiplicatively, with the original measured value 26 (operation measured gas value) to obtain a calibrated measured value: Calibrated measured value=original measured value 26/correction factor 28.

Figure 4:
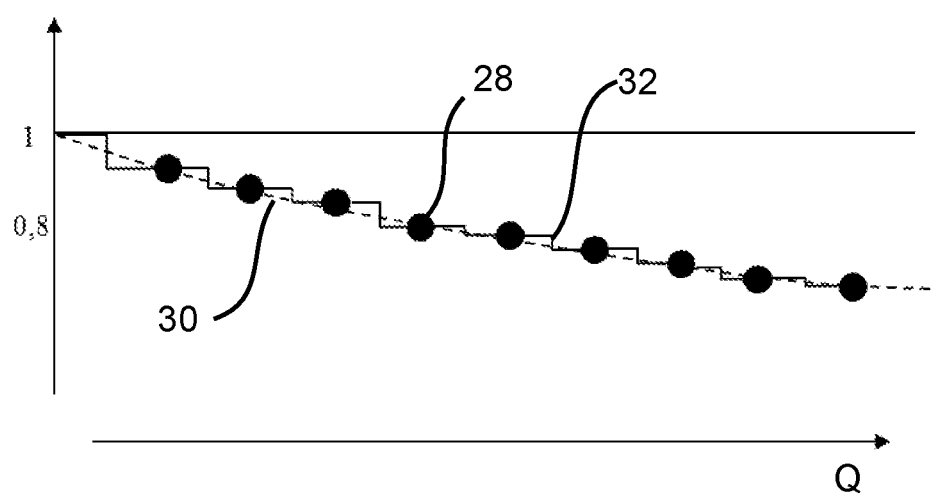
FIG. 4 is a graph showing a calibration function resulting on the basis of the calibration process.
Figure 5:
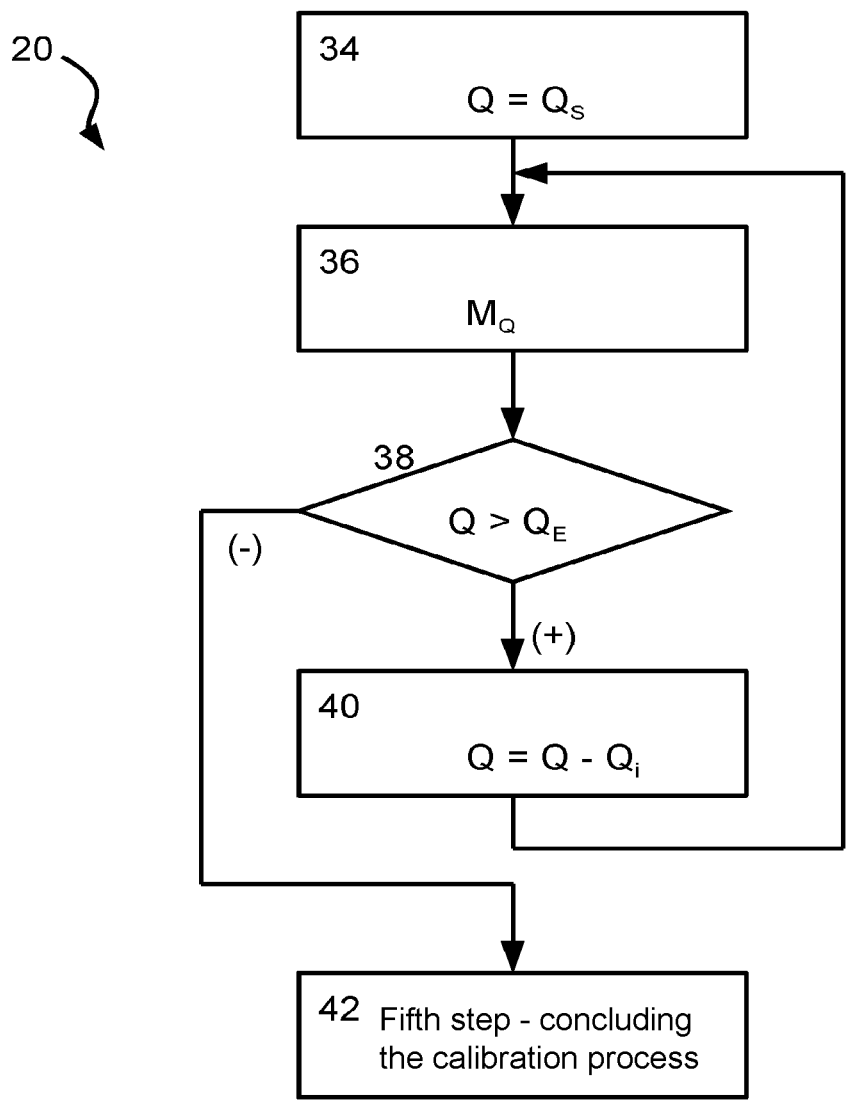
FIG. 5 is a flow chart showing the calibration process.

The view in FIG. 5 schematically shows in a simplified manner the course of a calibration process 20 of the type according to the invention. After the conclusion of a final installation of a gas sensor 10 and of a pump 12 in a tube system 14, for example, as is shown in FIG. 1, the calibration process 20 is started with a first step 34. The pump 12 is started and a test gas 16 is provided in this first step 34. The test gas concentration is maintained at a constant value during the calibration process 20. The pump 12 is started, for example, by selecting a corresponding speed, with a predefined or predefinable starting value for a high volume flow QS, by activating the pump 12, the test gas 16 is drawn into the tube system 14 and supplied to the gas sensor 10. A measurement is carried out in a second step 36 in the form of the detection of a measured value 26 (calibration measured gas value) by means of the gas sensor 10. For example, the end of a predefined or predefinable dead time is waited for until the detection or processing of a measured value 26 in order to ignore initial fluctuations in the measured value during an "adaptation time." In addition or as an alternative, it can be taken into consideration during the detection of a measured value 26 whether the measured value 26 is within an expectation frame and/or whether the fluctuations of the measured value 26 remain below a predefined or predefinable threshold value ΔQ during the measurement. A detected measured value 26 (calibration measured gas value) or a mean value formed from a plurality of detected measured values 26 (calibration measured gas values) is stored together with a calibration volume flow value coding (or expressing) the respective volume flow Q as a volume flow-dependent measured value (volume flow-dependent calibration measured gas value) $M_Q$. It is then checked in a third step 38 whether the volume flow Q is still higher than a predefined or predefinable final value $Q_E$ for the volume flow. If yes (branch "+"), the volume flow Q is reduced in a fourth step 40 corresponding to a predefined or predefinable increment $Q_i$ and then branched off to the second step 36, where the measurement is continued with the result of the determination of another volume flow-dependent measured value $M_Q$. If it is determined in the third step 38 that the volume flow Q has already reached the final value $Q_E$, the process is ended and is branched off to the fifth step 42 (branch "−") concluding the calibration process 20. The calibration function 32 (FIG. 4) is formed here as a calibration basis, for example, on the basis of all the calibration volume flow values detected within the framework of the calibration process 20 as well as of the volume flow-dependent measured values (volume flow-dependent calibration measured gas values) $M_Q$.

The normal measuring operation is then started. An original measured value (operation measured gas value) 26 is calibrated in the measuring operation by the gas sensor 10 as a function of a respective effective volume flow Q and an operation volume flow value coding (or expressing) this on the basis of the calibration basis, i.e., for example, with the value of the calibration function 32 instead of the respective volume flow Q (operation volume flow value).

The calibration process 20 is executed under the control of a control unit 44. This comprises, in the manner known basically per se, a processor in the form of or in the manner of a microprocessor as well as a memory 46, into which a control program 48, which is carried out during the operation of the control unit 44 by the processor thereof, is or has been loaded.

Figure 6:
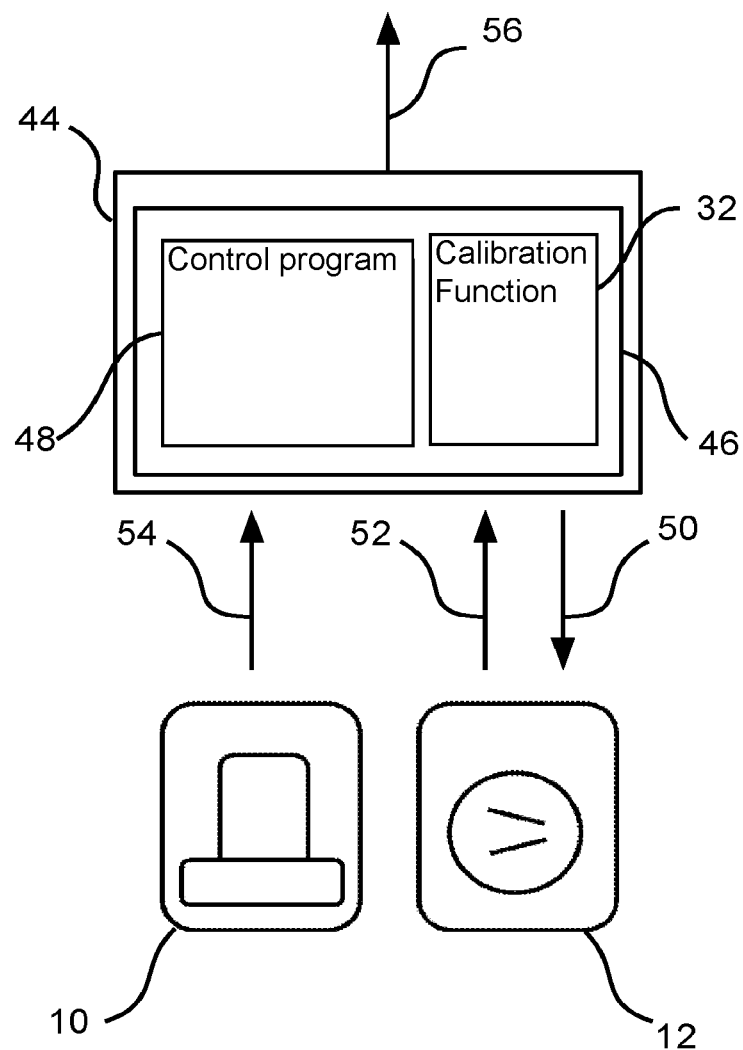
FIG. 6 is a schematic view showing a control unit with a control program loaded into a memory of the control unit as a means for executing the calibration process.

Such a control unit 44 is shown in a schematically simplified manner in the view in FIG. 6 and is optionally associated with the pump 12, for example, such that the pump 12 comprises the control unit 44 and the control unit 44 performs additional control and/or monitoring functions pertaining to the operation of the pump 12. Depending on the unit—pump 12 or gas sensor 10—to which the control unit 44 is assigned, data are transmitted from and/or to the respective unit, for example, internally, and the control unit 44 is connected to the respective other unit for communication in a manner that makes such data transmission possible and is known, in principle, per se.

During the calibration of a gas sensor 10, the control unit 44 determines, corresponding to the control program 48, the volume flow Q generated by the pump 12 during the operation. A control signal 50 is sent for this by the control unit 44 to the pump 12. During the regulation of the volume flow Q by means of the control unit 44, the latter receives from the pump 12 for the regulation an actual value signal 52, which codes an instantaneous value of the volume flow Q. The control signal 50 or the actual value signal 52 can be used during the calibration process as a volume flow value or as the basis for a volume flow value, namely, as a calibration volume flow value or as the basis for the calibration volume flow value. In addition or as an alternative, the possibility of detecting the respective effective volume flow Q by means of a corresponding sensor system and to use a corresponding measured value as a calibration volume flow value may be considered. The control unit 44 receives from the gas sensor 10 a measured value signal 54 representing a respective current original measured value 26 (calibration measured gas value).

The calibration process 20 is carried out by predefining a control signal 50 corresponding to the volume flow Q required within the framework of the calibration process 20 and analyzing the measured value signal 54 from the gas sensor 10, and the volume flow-dependent measured values $M_Q$ (volume flow-dependent calibration measured gas values) determined in the process are stored in the memory 46 of the control unit 44 together with the respective volume flow Q (calibration volume flow value). The volume flow-dependent measured values $M_Q$ and the respective corresponding volume flow Q form the calibration basis. The calibration function 32 is optionally determined from this and is likewise stored in the memory 46.

A gas to be measured is drawn in instead of a test gas 16 (FIG. 1) during the measuring operation. The measured value signal 54 of the gas sensor 10 now represents a measured gas concentration of this gas. The control unit 44 processes during the measuring operation the measured value signal 54 as a current measured value (operation measured gas value), on the hand, and, for example, the actual value signal 52 or—in case of an unregulated pump 12—the control signal 50 as a current volume flow Q (operation volume flow value), on the other hand. The control signal 50 or the actual value signal 52 may be used as a volume flow value or as the basis for a volume flow value in this case as well, i.e., during the measuring operation, namely, as an operation volume flow value during the measuring operation or as the basis for the operation volume flow value. The possibility of detecting the respective effective volume flow Q by means of a corresponding sensor system and of using a corresponding measured value as an operation volume flow value may likewise be considered here as well. Instead of drawing in a respective test gas 16 by means of the pump 12, it may also be considered to be possible here, in principle, that the pump 12 is inactive during the measuring operation and the test gas 16 reaches the gas sensor 10, for example, based on a pressure difference or of a volume flow that is independent from the pump 12 and is generated at a remote location from the gas sensor 10. The volume flow that is effective during the operation of the gas sensor 10 is in such a case provided by means of a corresponding sensor system and a measured value that can be obtained from this sensor system is used as an operation volume flow value. A volume flow-dependent correction factor 28 is obtained with the current volume flow Q (operation volume flow value) and the calibration basis, especially the calibration function 32, and the measured value is weighted with this correction factor 28. The weighted (calibrated) measured value is outputted as a measured gas value 56.

Figure 7:
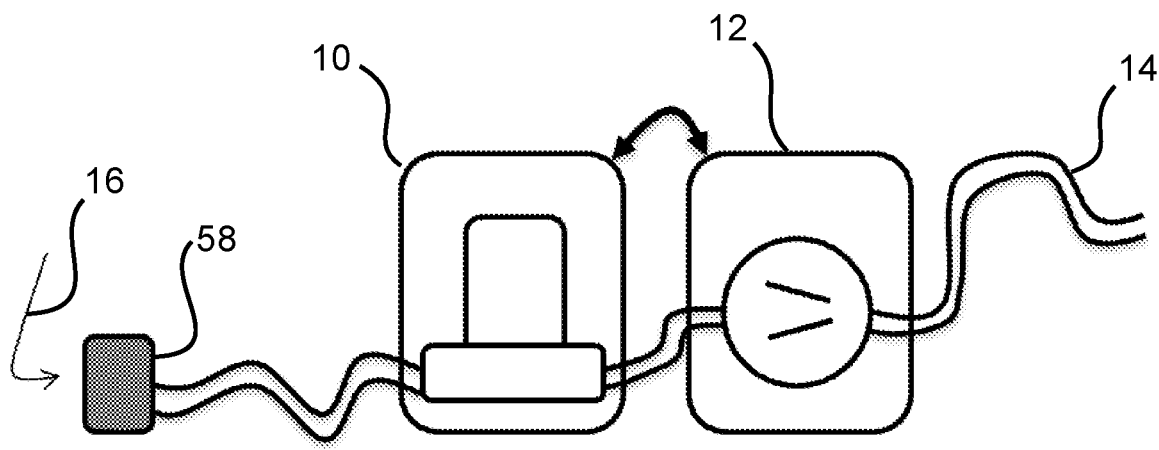
FIG. 7 is a schematic view showing a system with a gas sensor and with a pump as in FIG. 1, as well as with an input-side filter as an example of a flow resistance acting in the system.
Figure 8:
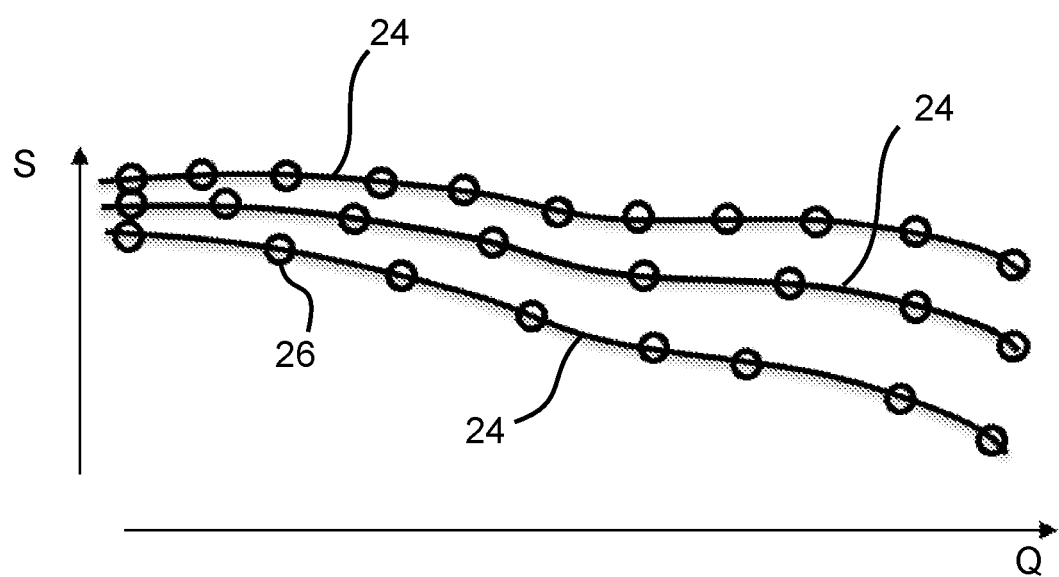
FIG. 8 is a schematic view showing characteristics resulting from different flow resistance values.

In addition to a respective effective volume flow Q (calibration volume flow value), the effect of a filter 58 (FIG. 7) is additionally detected in a special variant of the calibration process according to the invention. Filter-dependent or generally flow resistance-dependent measured value curves 24 and respective corresponding measured values 26 (calibration measured gas values) are thus obtained. The diagram in FIG. 8 shows in this respect three measured value curves 24 as an example, which were detected each for a tube system 14 with one and the same inlet-side filter 58, wherein the topmost measured value curve 24 represents the conditions in the case of a fresh filter 58 immediately after the installation thereof. The lower measured value curve 24 represents the conditions in the case of a clogged filter 58, and the measured value curve 24 between the upper measured value curve 24 and the lower measured value curve 24 represents the conditions in the case of an approximately half-clogged filter 58.

The measured values 26 (calibration measured gas values) are detected as described before on the basis of FIG. 3 and FIG. 5. The only difference is that the measured values 26 are optionally detected several times, namely, for different conditions, i.e., for example, once each for different effective flow resistances. A calibration basis, for example, a correction factor curve 30 and/or a calibration function 32 as is shown in FIG. 4, namely, a flow resistance-dependent calibration basis, especially a flow resistance-dependent correction factor curve 30 and/or a flow resistance-dependent calibration function 32, is obtained for each resulting measured value curve 24. This is (these are) provided with a category and stored under the corresponding category, for example, "fresh filter," "partially clogged filter," "clogged filter." A calibration basis, a correction factor 28, a correction factor curve 30 or a calibration function 32 is selected on the basis of measured values that are detected by means of a sensor system associated with the pump 12. The measured values are, in addition to the measured volume flow value already mentioned in the above explanation, a measured vacuum value. A respective effective flow resistance is obtained from these measured values in a manner that is known, in principle, per se, and a respective state of a filter 58 can, for example, be inferred from this. Consequently, a categorization is obtained on the basis of the measured values (measured volume flow value, vacuum measured value) for the current state of clogging of the filter 58, and a calibration basis, a correction factor 28, a correction factor curve 30 or a calibration function 32 can selected on this basis. It is, of course, possible to use more or fewer than three different categories.

A respective additional calibration basis or characteristic may optionally be detected corresponding to the measured value curve 24 shown in FIG. 3. Instead of the variation of the volume flow Q, which is carried out there (FIG. 3), for example, different temperatures, different relative humidities, etc., are then taken into consideration. A calibration basis thus determined is selected and a correction factor arising therefrom is determined on the basis of a measured value determined by means of a temperature and/or relative humidity sensor, etc. In case of independence of the factors influencing the original measured value 26 of the gas sensor 10, the respective resulting correction factors may be used multiplicatively. To detect a cross dependence, for example, volume flow and temperature, the volume flow Q is varied within the framework of the calibration process 20 and a variation of the temperature, which is embedded therein (or vice versa), is performed, so that, for example, a family of characteristics (not shown) is obtained as the calibration basis rather than an individual characteristic, as is shown in the measured value curve 24 shown in FIG. 3. A point is then determined in the family of characteristics during the measuring operation corresponding to the respective effective volume flow Q and a correction factor is derived from it.

Individual aspects of the specification being presented here, which are especially in the foreground, can thus be briefly summarized as follows: Proposed are a process for the operation of a gas sensor 10, which comprises a calibration, wherein a test gas 16 is drawn in by means of a pump 12 coupled with the gas sensor 10 and is supplied to the gas sensor 10, wherein different volume flows Q are generated by means of the pump 12 and respective volume flow-dependent measured values 26 (calibration measured gas values) are detected by means of the gas sensor 10, and wherein the volume flow-dependent measured values 26 are recorded together with the respective volume flow Q (calibration volume flow value), as well as a computer program acting as a control program 48 with an implementation of the process.

While specific embodiments of the invention have been shown and described in detail to illustrate the application of the principles of the invention, it will be understood that the invention may be embodied otherwise without departing from such principles.

APPENDIX

List of reference designations:

| | |
|---|---|
| 10 | Gas sensor |
| 12 | Pump |
| 14 | Tube system |
| 16 | Test gas |
| 18 | (Blank) |
| 20 | Calibration process |
| 22 | Volume flow curve |
| 24 | Measured value curve |
| 26 | Measured value |
| 28 | Correction factor |
| 30 | Correction factor curve |
| 32 | Calibration function |
| 34 | First step (of the calibration process) |
| 36 | Second step |
| 38 | Third step |
| 40 | Fourth step |
| 42 | Fifth step |
| 44 | Control unit |

-continued

List of reference designations:

| | |
|---|---|
| 46 | Memory |
| 48 | Control program |
| 50 | Control signal |
| 52 | Actual value signal |
| 54 | Measured value signal |
| 56 | Measured gas value |
| 58 | Filter |

What is claimed is:

1. A process for operating a gas sensor, the process comprising the steps of:
drawing a test gas into the gas sensor to supply the test gas to the gas sensor by a pump coupled with the gas sensor;
generating different volume flows by the pump;
detecting respective volume flow-dependent measured values by the gas sensor;
recording the volume flow-dependent measured values together with the respective volume flow;
determining correction factors or a calibration function as a calibration basis, based on the volume flow-dependent measured values and the respective corresponding volume flow;
detecting a measured value supplied by the gas sensor and an effective volume flow; and
correcting the detected measured value based on the detected effective volume flow as well as based on the volume flow-dependent measured values determined within a framework of a calibration process, during a measuring operation of the gas sensor.

2. A process in accordance with claim 1, wherein the detected measured value is corrected by using the calibration function or the correction factors to calibrate the detected measured value by determining, as a function of the detected effective volume flow, a correction factor best fitting the effective volume flow or a value of the calibration function, which value belongs to the correction factor, and calibrating the detected measured value with the correction.

3. A process in accordance with claim 1, wherein a volume flow is initially generated corresponding to a predefined starting value to generate different volume flows by the pump and wherein the volume flow is increased or decreased starting from the starting value until a predefined target value is reached.

4. A process in accordance with claim 3, wherein the volume flow is increased or decreased stepwise at a predefined or predefinable increment starting from the starting value until the target value is reached.

5. A process in accordance with claim 3, wherein the starting value for the volume flow is higher than the target value and wherein the volume flow is reduced starting from the starting value until the target value is reached.

6. A process in accordance with claim 1, wherein the volume flow-dependent measured values detected for the calibration basis are detected for different flow resistances.

7. A process in accordance with claim 1, wherein the calibration basis is selected based on the detected volume flow and wherein the detected measured value is corrected based on the selected calibration basis.

8. A process in accordance with claim 1, wherein the volume flow-dependent measured values, providing the calibration basis, are detected when the gas sensor is in an installation situation intended for a subsequent operation of the gas sensor.

9. A process in accordance with claim 1, wherein the steps are implemented with a control program executed by means of a control unit operatively connected to the gas sensor and the pump.

10. A system comprising:
a gas sensor;
a pump connected fluidically to the gas sensor;
a control unit configured to implement a process comprising the steps of:
drawing a test gas into the gas sensor to supply the test gas to the gas sensor by means of a pump coupled with the gas sensor;
generating different volume flows by the pump;
detecting respective volume flow-dependent measured values by means of the gas sensor;
recording the volume flow-dependent measured values together with the respective volume flow;
determining correction factors or a calibration function as a calibration basis, based on the volume flow-dependent measured values and the respective corresponding volume flow;
detecting a measured value supplied by the gas sensor and an effective volume flow; and
correcting the detected measured value based on the detected effective volume flow as well as based on the volume flow-dependent measured values determined within a framework of a calibration process, during a measuring operation of the gas sensor.

11. A system according to claim 10, wherein the control unit is configured by providing the control unit with a control program with which the control unit executes the process steps.

12. A system in accordance with claim 10, wherein the detected measured value is corrected by using the calibration function or the correction factors to calibrate the detected measured value by determining, as a function of the detected effective volume flow, a correction factor best fitting the effective volume flow or a value of the calibration function, which value belongs to the correction factor, and calibrating the detected measured value with the correction.

13. A system in accordance with claim 10, wherein a volume flow is initially generated corresponding to a predefined starting value to generate different volume flows by the pump and wherein the volume flow is increased or decreased starting from the starting value until a predefined target value is reached.

14. A system in accordance with claim 13, wherein the volume flow is increased or decreased stepwise at a predefined or predefinable increment starting from the starting value until the target value is reached.

15. A system in accordance with claim 13, wherein the starting value for the volume flow is higher than the target value and wherein the volume flow is reduced starting from the starting value until the target value is reached.

16. A system in accordance with claim 10, wherein the volume flow-dependent measured values detected for the calibration basis are detected for different flow resistances.

17. A system in accordance with claim 10, wherein the calibration basis is selected based on the detected volume flow and wherein the detected measured value is corrected based on the selected calibration basis.

18. A system in accordance with claim 10, wherein the volume flow-dependent measured values, providing the calibration basis, are detected when the gas sensor is in an installation situation intended for a subsequent operation of the gas sensor.

19. A control program in the form of a computer program with program code to cooperate with a control unit to execute a process for operating a gas sensor, the process comprising the steps of:
drawing a test gas into the gas sensor to supply the test gas to the gas sensor by means of a pump coupled with the gas sensor;
generating different volume flows by the pump;
detecting respective volume flow-dependent measured values by means of the gas sensor;
recording the volume flow-dependent measured values together with the respective volume flow;
determining correction factors or a calibration function as a calibration basis, based on the volume flow-dependent measured values and the respective corresponding volume flow;
detecting a measured value supplied by the gas sensor and an effective volume flow; and
correcting the detected measured value based on the detected effective volume flow as well as based on the volume flow-dependent measured values determined within a framework of a calibration process, during a measuring operation of the gas sensor.

20. A control program in accordance with claim 19, wherein:
the detected measured value is corrected by using the calibration function or the correction factors to calibrate the detected measured value by determining, as a function of the detected effective volume flow, a correction factor best fitting the effective volume flow or a value of the calibration function, which value belongs to the correction factor, and calibrating the detected measured value with the correction; and
a volume flow is initially generated corresponding to a predefined starting value to generate different volume flows by the pump and wherein the volume flow is increased or decreased starting from the starting value until a predefined target value is reached.

* * * * *